United States Patent
Cowe et al.

(10) Patent No.: US 10,426,898 B2
(45) Date of Patent: Oct. 1, 2019

(54) RETRACTABLE NEEDLE ASSEMBLIES

(71) Applicant: Owen Mumford Limited, Oxford (GB)

(72) Inventors: Toby Cowe, Oxford (GB); Oliver Anderson, Oxford (GB); Jack Calvert, Oxford (GB)

(73) Assignee: Owen Mumford Limited (GB)

( * ) Notice: Subject to any disclaimer, the term of this patent is extended or adjusted under 35 U.S.C. 154(b) by 23 days.

(21) Appl. No.: 15/500,769

(22) PCT Filed: Aug. 3, 2015

(86) PCT No.: PCT/GB2015/052243
§ 371 (c)(1),
(2) Date: Jan. 31, 2017

(87) PCT Pub. No.: WO2016/020662
PCT Pub. Date: Feb. 11, 2016

(65) Prior Publication Data
US 2017/0209653 A1 Jul. 27, 2017

(30) Foreign Application Priority Data

Aug. 4, 2014 (GB) .................................... 1413777.2
Nov. 28, 2014 (GB) .................................... 1421126.2
May 11, 2015 (GB) .................................... 1507993.2

(51) Int. Cl.
*A61M 5/32* (2006.01)

(52) U.S. Cl.
CPC .......... *A61M 5/3221* (2013.01); *A61M 5/321* (2013.01); *A61M 5/322* (2013.01);
(Continued)

(58) Field of Classification Search
CPC .. A61M 5/3221; A61M 5/3205; A61M 5/321; A61M 5/322; A61M 5/3278;
(Continued)

(56) References Cited

U.S. PATENT DOCUMENTS

| 4,188,950 | A | * | 2/1980 | Wardlaw | ............. | A61M 5/2033 |
| | | | | | | 604/111 |
| 4,266,544 | A | * | 5/1981 | Wardlaw | ............. | A61M 5/3278 |
| | | | | | | 604/110 |

(Continued)

FOREIGN PATENT DOCUMENTS

| WO | 00/56384 A | 9/2000 |
| WO | 2014/003632 A1 | 1/2014 |

OTHER PUBLICATIONS

International Search Report and Written Opinion issued in corresponding PCT Application No. PCT/GB2015/052243, dated Oct. 15, 2015, 14 pages.

(Continued)

*Primary Examiner* — Manuel A Mendez
(74) *Attorney, Agent, or Firm* — Quarles & Brady LLP

(57) ABSTRACT

A retractable needle assembly comprises a body portion, a needle having a patient end and being movable between an operational position in which the needle extends along a longitudinal needle axis with the patient end projecting forwardly from said body portion, and a safe position in which said patient end is retracted into said body portion, a deflector element rotatable about a deflector rotary axis generally perpendicular to said needle axis to move the needle to its safe position, and a manually operated deflector lever connected to or forming part of said deflector element, the deflector lever projecting from said body portion and intersecting a plane perpendicular to the deflector rotary axis and containing the needle axis.

16 Claims, 14 Drawing Sheets

(52) U.S. Cl.
CPC ........ *A61M 5/3205* (2013.01); *A61M 5/3278* (2013.01); *A61M 2005/3284* (2013.01); *A61M 2207/00* (2013.01)

(58) Field of Classification Search
CPC ........ A61M 2005/3284; A61M 5/2033; A61M 5/3202; A61M 5/3216; A61M 5/326; A61M 5/20; A61M 25/0631; A61M 5/3245; A61M 5/002; A61M 5/158; A61M 5/3271; A61M 25/0637; A61M 25/0606; A61M 5/14546; A61M 5/3204; A61B 5/150656; A61B 17/0469
USPC ........................................ 604/272, 110, 111
See application file for complete search history.

(56) References Cited

U.S. PATENT DOCUMENTS

| | | | | |
|---|---|---|---|---|
| 4,664,259 A | * | 5/1987 | Landis | A61M 5/3216 |
| | | | | 206/364 |
| 5,084,019 A | * | 1/1992 | Gartz | A61M 5/322 |
| | | | | 604/110 |
| 5,084,020 A | * | 1/1992 | Gartz | A61M 5/322 |
| | | | | 604/110 |
| 5,476,106 A | | 12/1995 | Gartz | |
| 5,891,093 A | * | 4/1999 | Dysarz | A61M 5/32 |
| | | | | 604/110 |
| 6,010,481 A | | 1/2000 | Lee | |
| 6,183,439 B1 | * | 2/2001 | Nakajima | A61M 5/3278 |
| | | | | 128/919 |
| 6,186,979 B1 | * | 2/2001 | Dysarz | A61M 5/3278 |
| | | | | 128/898 |
| 2002/0062107 A1 | | 5/2002 | Parmigiani | |

OTHER PUBLICATIONS

United Kingdom Search Report issued in corresponding United Kingdom Patent Application No. 1413777.2, dated Feb. 18, 2015, 5 pages.

\* cited by examiner (a)

(b)

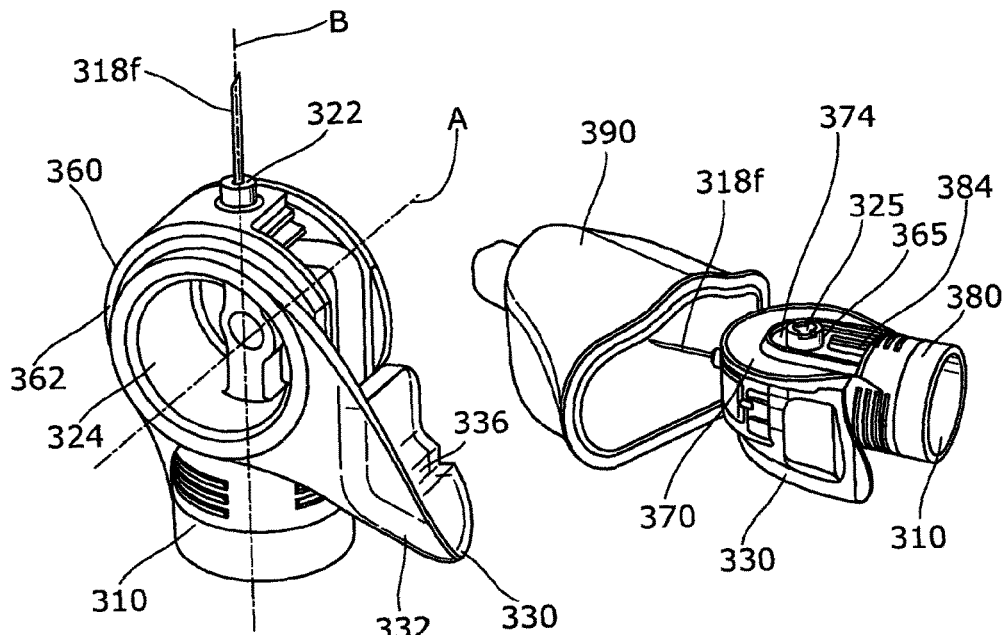
Fig. 13(a)
Fig. 13(b)
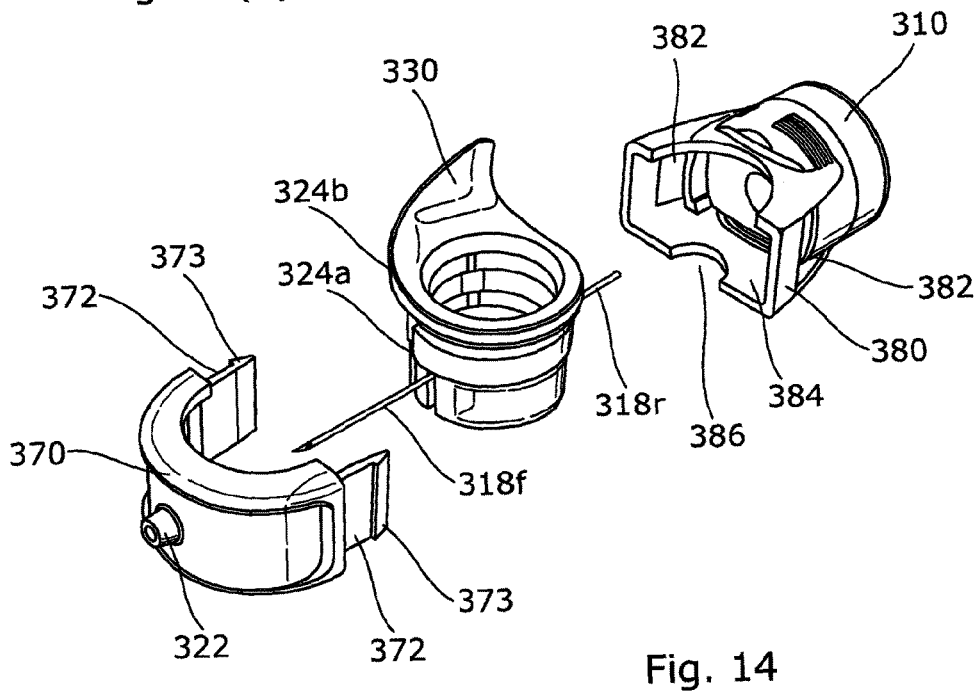
Fig. 14

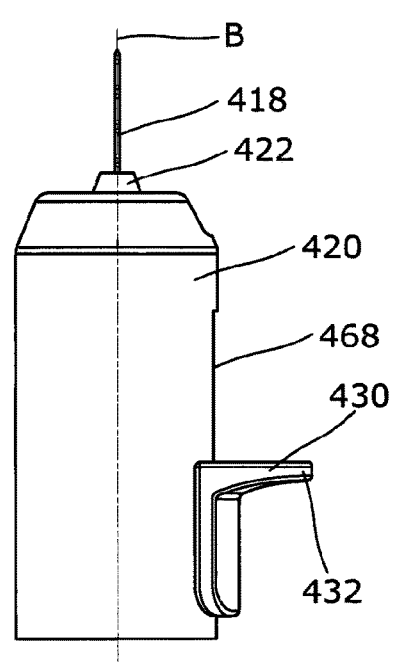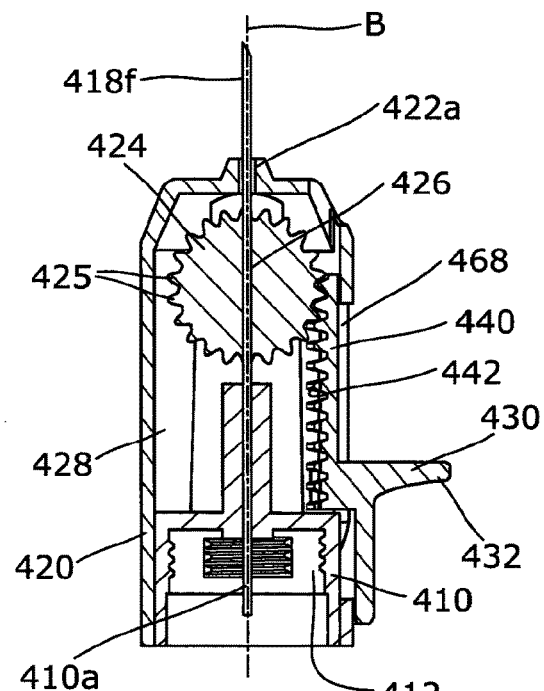
Fig. 19(a)  Fig. 19(b)
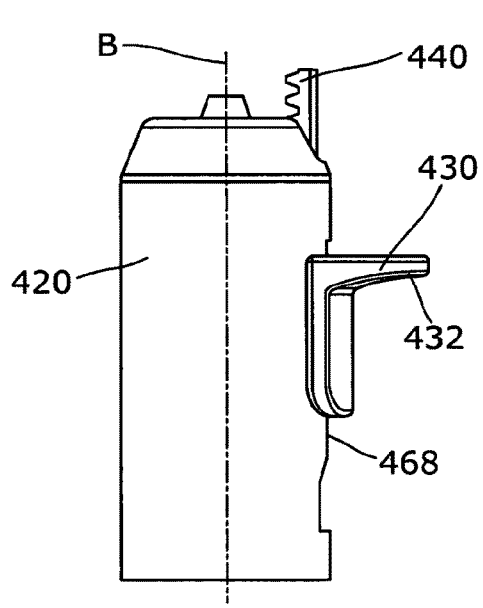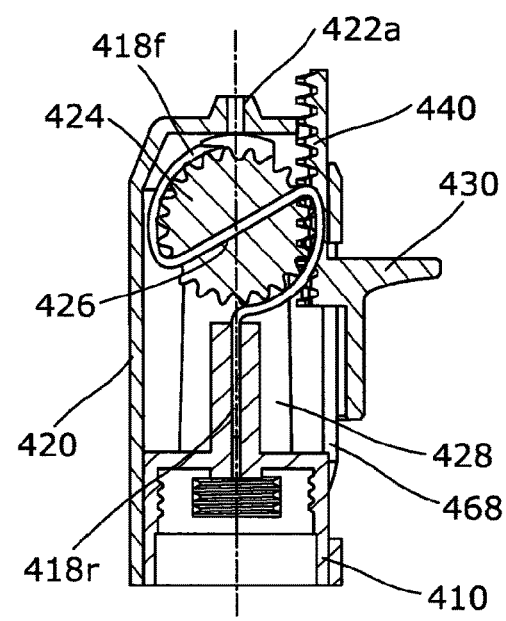
Fig. 20(a)  Fig. 20(b)

RETRACTABLE NEEDLE ASSEMBLIES

CROSS-REFERENCE TO RELATED APPLICATIONS

This application represents the U.S. National Stage of International Application No. PCT/GB2015/052243 filed Aug. 3, 2015, which is incorporated by reference in its entirety and is based on, claims priority to, and incorporates herein by reference in their entireties, British Patent Application Serial Nos. GB 1413777.2, filed Feb. 10, 2014, GB 1421126.2, filed Nov. 28, 2014, and GB 1507993.2, filed May 11, 2015 and entitled, "Retractable Needle Assemblies."

This invention relates to retractable needle assemblies for attachment to, or forming an integral part of, a syringe or cartridge arrangement or other injection device.

There are many situations in which an injection needle is required to be shielded after use to prevent the risk of needle stick injury. This applies not only to single use devices such as disposable syringes and the like, but also to multiple use devices such as cartridges where a disposable needle is secured, e.g. by screwing or other suitable connection action, into a cartridge or adaptor and replaced for each subsequent injection. This is especially important in clinics and hospitals where the user is injected by a clinician, where the risk of cross-infection is greater.

U.S. Pat. No. 5,476,106 discloses an arrangement in which a cannula extends diametrically through a reel mounted in a housing. The reel may be rotated by means of a flat twist handle that is coplanar with the axis of the cannula and rotates about an axis in the same plane. In order to destroy the cannula after use the twist handle is twisted around its axis several times to wind the cannula around the reel and to draw it into the housing.

A problem with this arrangement is that it encourages two-handed use by the user holding the medical instrument in one hand and twisting the twist handle by several revolutions with the other. When grabbing the twist handle, the user is likely to approach it from the front or side, thus increasing the risk of inadvertent needle stick injury. Also, the user will need to grip and release the twist handle several times when retracting the cannula and thus increases the likelihood of an accidental needle stick injury.

We have therefore designed a retractable needle assembly with a manually operated lever that is designed to encourage single-handed use of the device and where it is possible for the user to render the needle safe by flicking the lever forward from the rear side, using the thumb of the hand holding the device.

Accordingly, in one aspect, this invention provides a retractable needle assembly comprising:
a body portion;
a needle having a patient end and being movable between an operational position in which the needle extends along a longitudinal needle axis with the patient end projecting forwardly from said body portion, and a safe position in which said patient end is retracted into said body portion;
a deflector element rotatable about a deflector rotary axis generally perpendicular to said needle axis to move the needle to its safe position, and
a manually operated deflector lever connected to or forming part of said deflector element, the deflector lever projecting from said body portion and intersecting a plane perpendicular to the deflector rotary axis and containing the needle axis.

In this arrangement, because the deflection lever intersects the plane perpendicular to the deflector rotary axis and containing the needle, the lever will typically lie in the path between the user's thumb and the needle, thereby providing temporary guarding of the thumb and also ensuring that the user does not expose themselves to significant risk of needle stick injury when retracting the needle.

Typically the deflector lever straddles said plane, with portions thereof lying to either side of the plane. In one arrangement, the deflector lever is generally symmetric about said plane. In this arrangement, the user may render the assembly safe by moving their thumb linearly down the body of the syringe, cartridge or other injection device, and no twisting action is required.

Conveniently, said deflector element comprises a rotary element through which an intermediate portion of said needle extends and about a circumference which the needle is wound when the deflector element is rotated. The deflector lever initially may take any suitable position; for example, it may project transversely relative to the needle axis so that it stands proud of the syringe, cartridge or injection device and may be contacted in use by a user sliding their thumb down the body of the device.

It will be appreciated that the user may instead place the projecting deflector lever against a suitable surface to rotate it to move the needle to the safe position.

In one arrangement, the deflector lever projects at an angle of at least 90° to the patient end of the needle.

The lever may be integrally formed with the deflector. The deflector may include an inner portion and an outer portion. In an assembled configuration the inner portion may be located within the body portion and the outer portion may be located outside the body portion. The deflection lever may extend from the outer portion of the deflector.

The deflector inner portion may include a rotary element through which an intermediate portion of the needle extends. The deflector inner portion may include a bore or channel for receiving an intermediate portion of the needle. The intermediate portion of the needle may be secured in the deflector inner portion. The intermediate portion of the needle may be secured in the bore or channel. The deflector inner portion may include a cylindrical outer surface, about which the needle is wound when the deflector is rotated.

The deflector may, for example, be arranged so as to snap fit into a recess or cavity within the body portion. The deflector may be movably retained within the body portion. The deflector may, for example, be able to freely rotate when snap fitted into the body.

The body portion may include a needle channel or bore provided in the cavity or recess, through which an intermediate portion of the needle extends. The needle channel may be integrally formed with or secured to the body portion. The intermediate portion of the needle may be secured in the needle channel.

The deflector inner portion may include a substantially annular element which surrounds and is rotatable about a needle channel provided in the recess or cavity. The deflector inner portion may include a substantially annular element, about which forward and rear portions of the needle are wound when the deflector is rotated. The substantially annular element may include a pair of circumferentially opposed cut-outs or bores for receiving the needle.

The body portion may be a housing. The body portion may comprise two housing portions. The body portion may comprise a forward housing portion and a rear housing portion. Alternatively, the body portion may comprise left and right body portions.

The two housing portions may be configured to be assembled or connected together to form a circular recess or cavity which extends into the body portion. The two housing portions may snap fit together. The deflector may be movably retained between the two body portions. The deflector may, for example, be able to freely rotate when retained between the two body portions.

In an assembled configuration the deflector inner portion may be located within a cavity or recess formed by the two housing portions. The deflector inner portion may include a rotary element through which an intermediate portion of the needle extends. An intermediate portion of the needle may be secured in a channel or bore formed in the rotary element. The body portion may comprise a substantially cylindrical housing. The housing may be connected to a hub portion. The housing may define an inner chamber. The deflector element may be rotatably mounted within the chamber.

The housing may include a longitudinal slot. The deflector lever may include an inner portion located within the housing chamber. The deflector lever may include an outer portion defining an operating flap which extends through the housing slot and projects at an angle perpendicular to the needle axis B.

The deflector element may be connected to the deflector lever via a gear arrangement. The deflector element may be connected to the deflector lever via a rack and pinion arrangement. The deflector element may comprise a gear wheel. The deflector lever may comprise a linear gear or rack for engaging the gear wheel. The deflector lever may be slideable in a longitudinal direction.

Advantageously the circumference of the rotary element or the substantially annular element and the length of the needle are selected so that the patient end of the needle is retracted into the housing upon rotation of the deflector by an angular amount of 270° or less, preferably less than 180°, more preferably less than 120° and, ideally, by about 90°.

The needle may be a single ended needle with an exposed patient end that is retracted by operation of said deflector element or it may be double ended with a non-patient end opposite the patient end configured in use for piercing a seal element. In this instance the deflector element may cause both ends of the needle to retract into the body portion upon rotation thereof. Alternatively, the non-patient end may be fixed, with the deflector element causing the patient end only to retract.

Conveniently, the assembly includes a non-return mechanism for preventing movement of the lever in a direction opposite to that which causes retraction, over at least part of its arc of rotation.

The non-return mechanism may be configured to hold or retain the deflector element when the needle is in its safe position. The non-return mechanism may include an engaging feature provided on one of the body or the deflector element, which engages with a cooperating feature provided on the other of the body or the deflector element.

Conveniently, the assembly includes a snap-action end stop which operates to permanently capture the lever at the end of a retraction stroke and to provide a sensory indication to the user that the needle is safe.

The assembly may include cooperating features which are configured to releasably hold or retain the deflector when the needle is in its operational position.

The needle assembly may be provided with a removable cap.

In another aspect, this invention provides a moulded plastics item for connecting around a needle to provide a retractable needle assembly. Preferably said item includes first and second drum portions configured to be brought together in use about a needle to provide a drum with a needle extending therethrough.

The item may also include first and second connector portions configured to be brought together in use to form a connector to allow said needle assembly to be connected in use directly or indirectly to at least one of a syringe, cartridge, or injection device.

The item may also include first and second housing portions configured to be brought together in use to provide a housing defining a generally circular opening in which in use said drum is constrained to rotate.

Conveniently said first and second drum portions are connected to respective first and second housing portions by frangible webs.

In the typical manufacture of a needle assembly such as our Unifine® product, a plastics hub is injection moulded leaving a bore for the needle, and, after injection moulding, a needle is inserted into the bore and then held there by application of an adhesive material. This assembly requires precise alignment between the needle and the bore, and this is a delicate process given the outer diameter of a typical needle may be of the order of 0.25 mm.

We have therefore developed a method and assembly in which a needle housing is manufactured by moulding a component that defines two or more integral housing portions that may be folded or hinged to make up the final housing, and then folding, hinging or enclosing the moulding around a needle.

In another aspect, there is provided a moulded plastics preform having integral hingeable housing portions adapted in use to be folded about a needle and interconnected to form a needle assembly having a connector for connection to a syringe cartridge or other injection device.

In yet another aspect, there is provided a method of manufacturing a needle assembly which comprises providing an integrally moulded plastics item defining integral first and second body portions hingedly attached to each other, and closing said body portions about needle to provide said needle assembly.

Whilst the invention has been described above, it extends to any inventive combination of the features set out in the following description or claims or drawings.

The invention may be performed in various ways, and three embodiments thereof will now be described in detail, reference being made to the accompanying drawings, in which.

Figure 1:
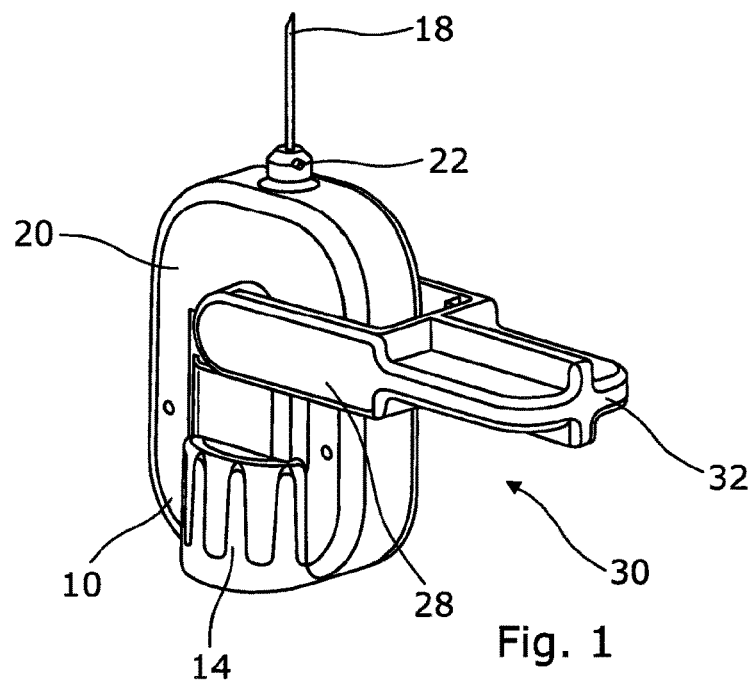
FIG. 1 is a perspective view of a first embodiment of retractable needle assembly in accordance with the invention, with the needle being in its exposed condition ready to deliver an injection.
Figure 2:
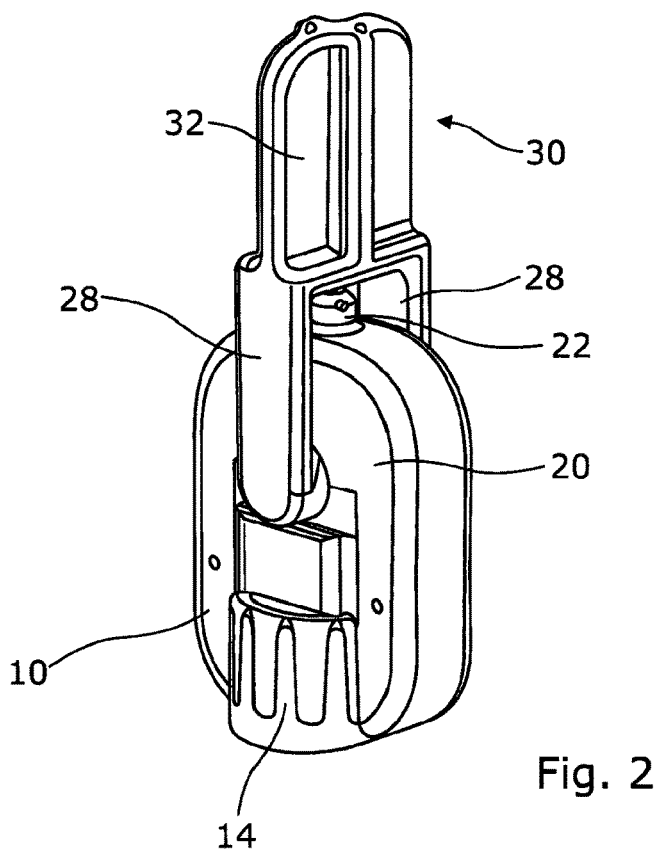
FIG. 2 is a view similar to FIG. 1 except showing the retractable needle assembly with the deflector lever rotated through 90° to retract the patient end of the needle inside the needle housing.

FIGS. 3(a) to (d) are sectional views of the embodiment of FIGS. 1 and 2 shown in the pre-injection position, partly retracted, fully retracted and final positions, respectively;

FIGS. 4(a) and (b) are sketch side views showing the thumb position of a user shielded from and ready to retract the needle.

Figure 5:
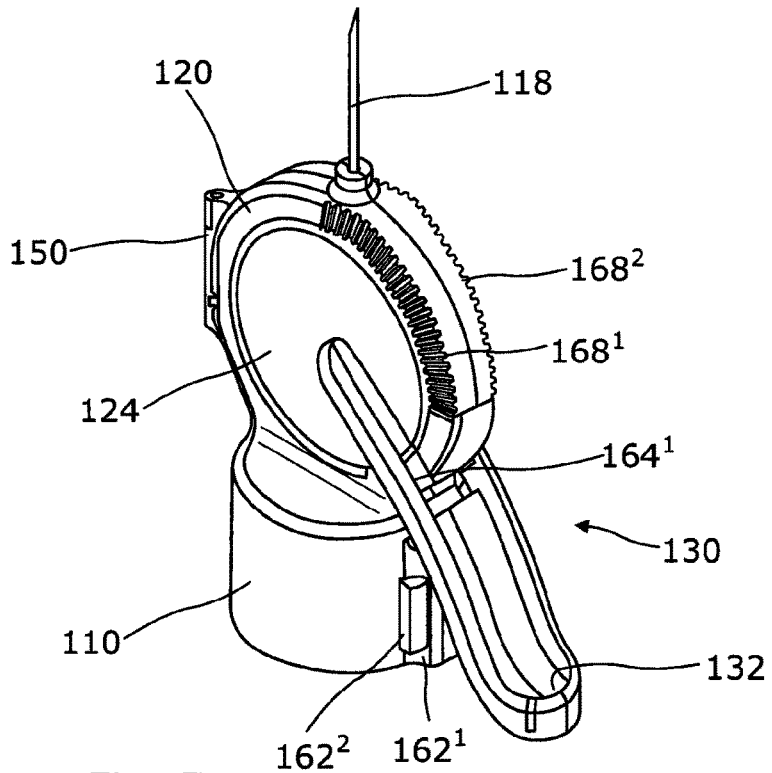
Figure 8:
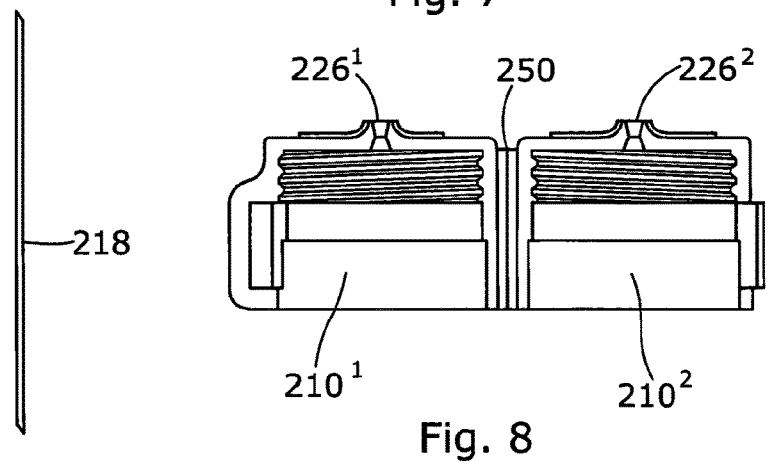

FIG. 5 is a perspective view of a second embodiment of retractable needle assembly in accordance with this invention, with the needle exposed prior to an injection;

FIGS. 6(a) and (b) are views on the inner and outer faces respectively of an injection moulded preform prior to being folded around and clipped together around a needle to form the retractable needle assembly shown in FIG. 5;

FIGS. 7(a) and (b) are views on the outer and inner surfaces respectively of the injection moulded preform;

FIG. 8 is a view of a third embodiment of a needle assembly in accordance with the invention, in an unfolded condition.

Figure 9A:
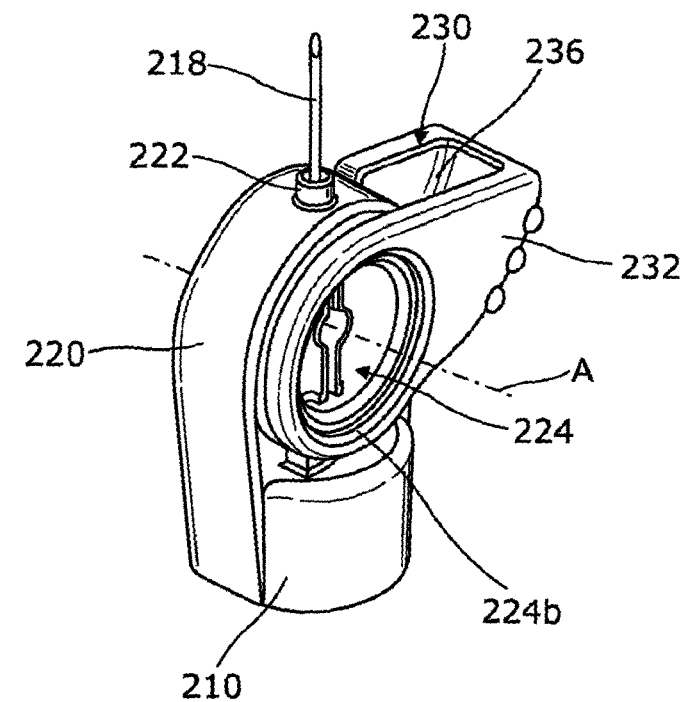
Figure 9B:
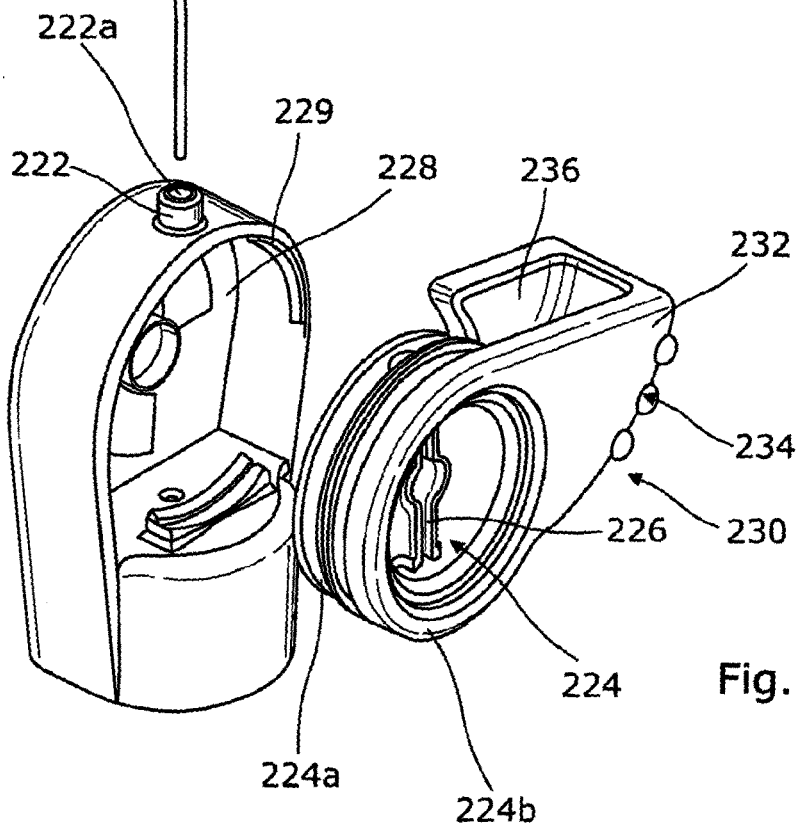
Figure 10A:
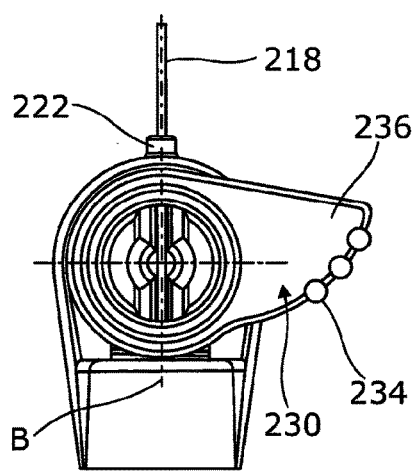
Figure 11A:
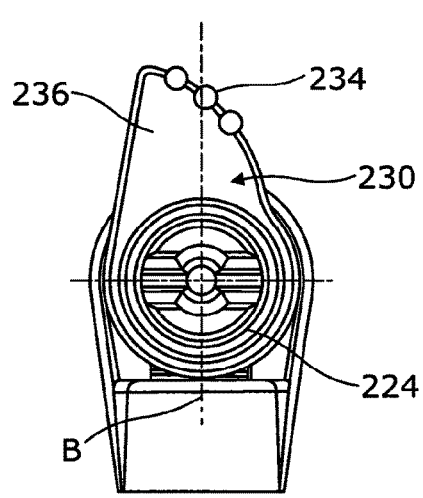
Figure 12A:
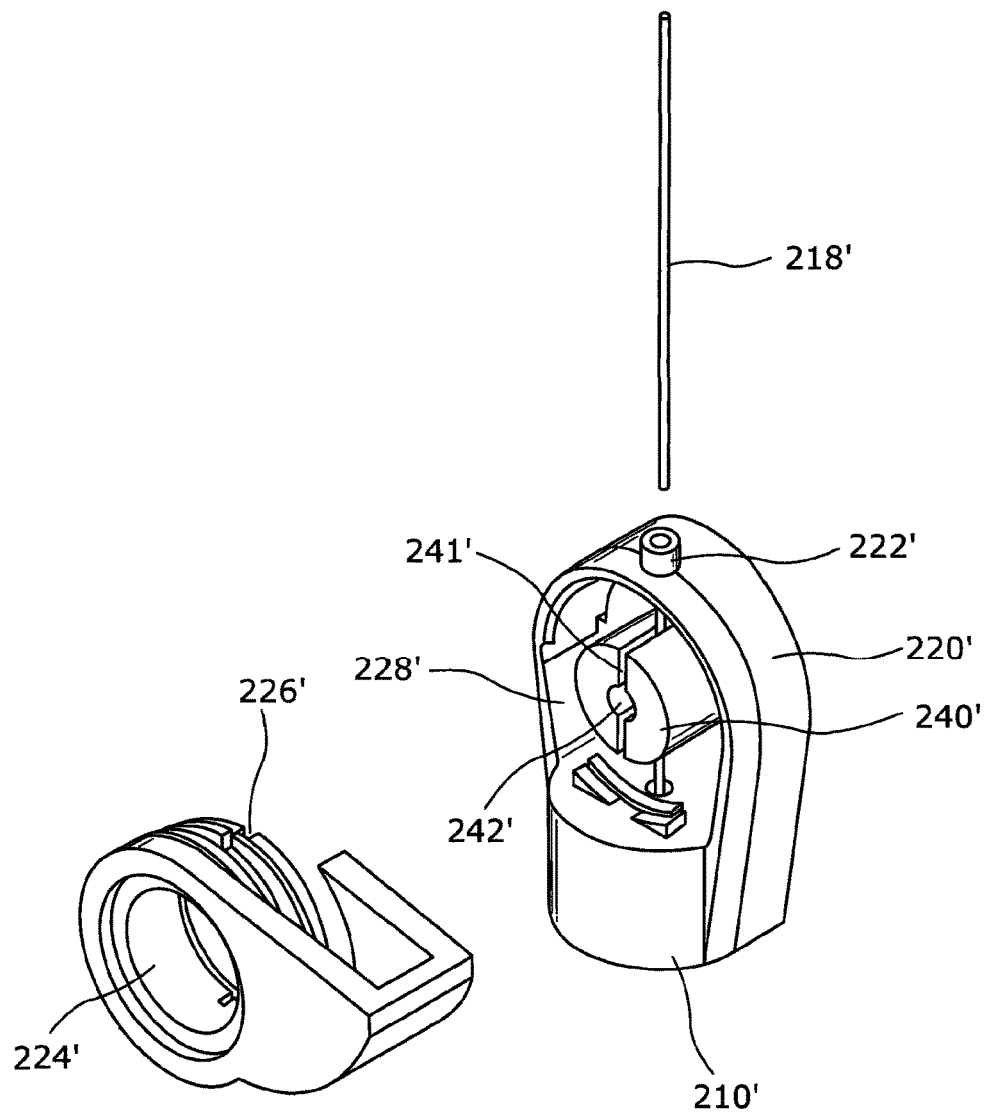
Figure 12B:
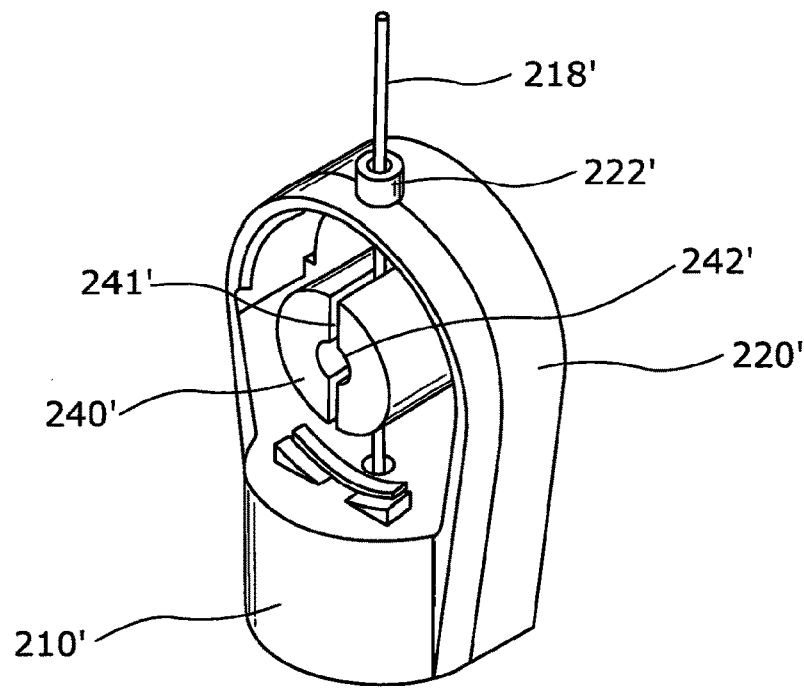
Figure 12C:
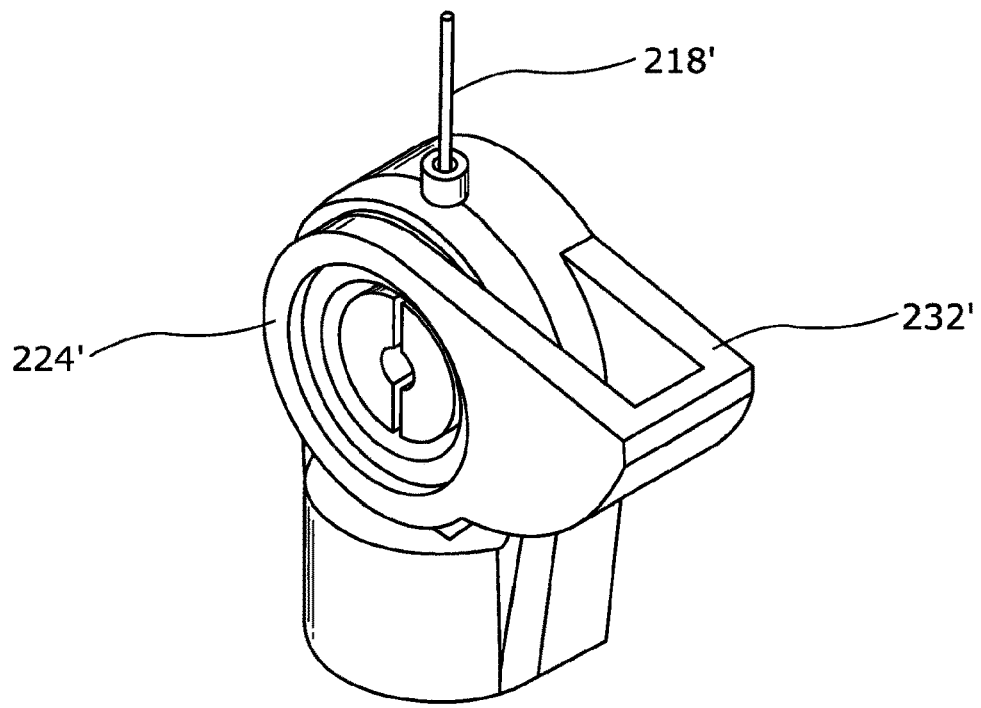
Figures 15A, 15B:
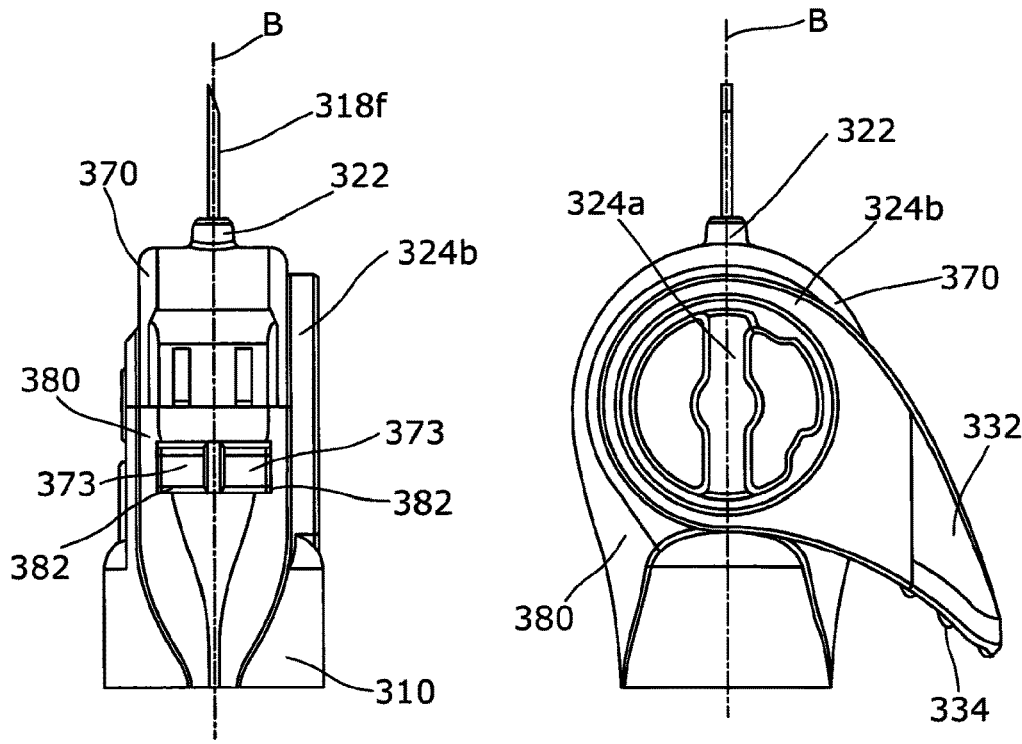
Figures 16A, 16B:
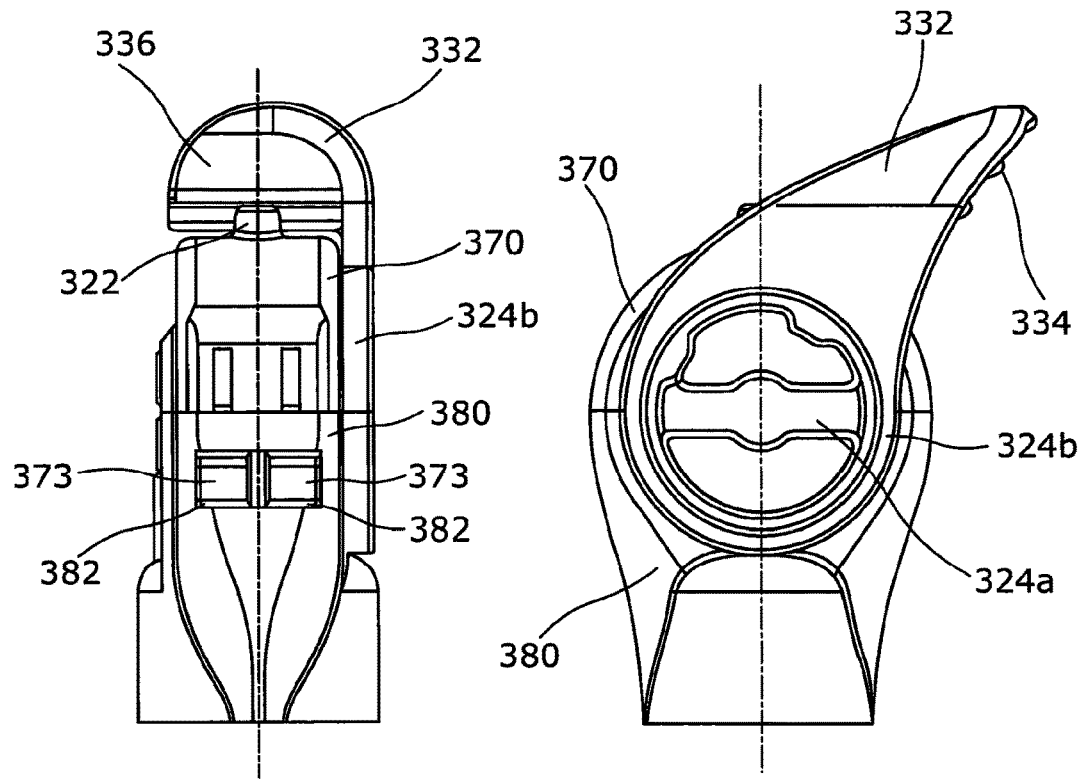
Figure 16C:
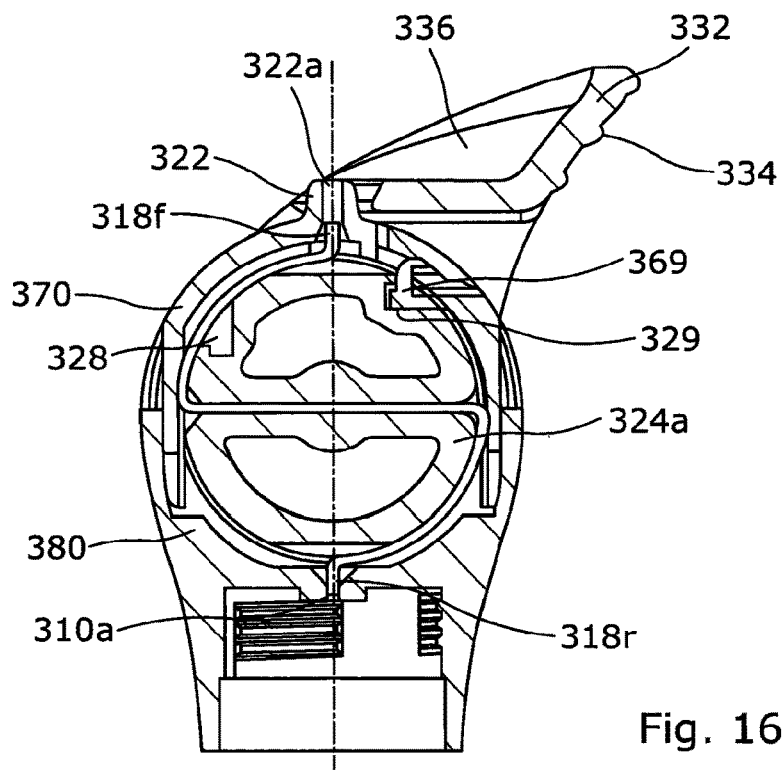
Figure 17:
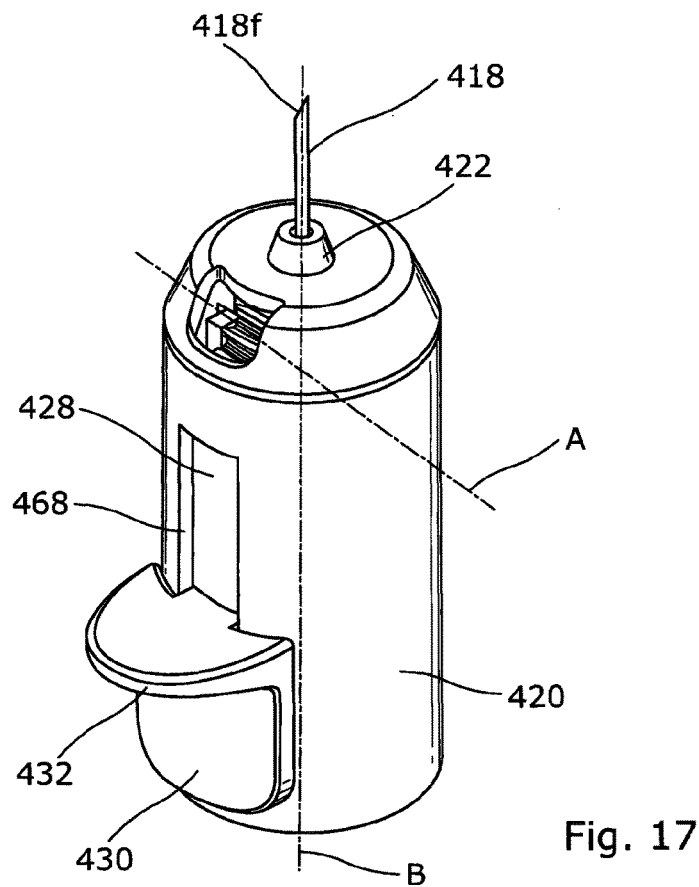

FIG. 9(a) is a perspective view of a fourth embodiment of a needle assembly in accordance with the invention with the needle exposed prior to an injection;

FIG. 9(b) is an exploded view of the components of FIG. 9(a);

FIGS. 10(a) and (b) show a side view of and a cross-section through the needle assembly of FIG. 9(a) with the needle exposed prior to an injection;

FIGS. 11(a) and (b) show a side view of and a cross-section through the assembly of FIG. 9(a) with the deflector lever rotated to retract the patient end of the needle inside the needle housing;

FIG. 12(a) shows an exploded view of a modified version of the embodiment of FIG. 9;

FIG. 12 (b) shows a partially assembled view of the embodiment of FIG. 12(a);

FIG. 12(c) show a perspective view of the embodiment of FIG. 12(a) in a fully assembled state with the needle exposed prior to an injection;

FIG. 13(a) is a perspective view from a first side of a fifth embodiment of a needle assembly in accordance with the invention with the needle exposed prior to an injection;

FIG. 13(b) is a perspective view from the rear of the retractable needle assembly of FIG. 13(a) with a safety cap;

FIG. 14 is an exploded view of the components of FIG. 13(a);

FIGS. 15(a), (b) and (c) show side views and a cross-section through the needle assembly of FIG. 13(a) with the needle exposed prior to an injection;

FIGS. 16(a), (b) and (c) show side views and a cross-section through the needle assembly of FIG. 13(a) with the deflector lever rotated to retract the patient end of the needle inside the needle housing;

FIG. 17 is a perspective view from a first side of a sixth embodiment of a needle assembly in accordance with the invention with the needle exposed prior to an injection.

Figure 18:
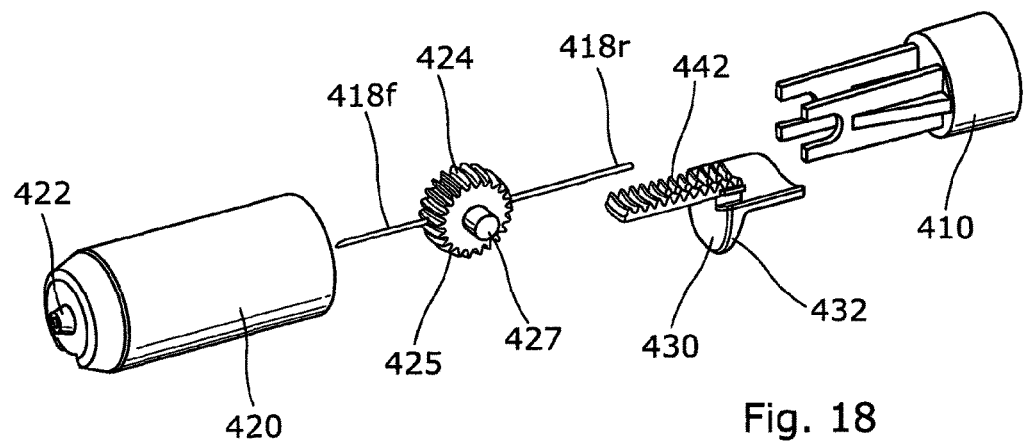

FIG. 18 is an exploded view of the components of FIG. 17;

FIGS. 19(a) and (b) show a side view and a cross-section through the needle assembly of FIG. 17 with the needle exposed prior to an injection; and FIGS. 20(a) and (b) show a side view and a cross-section through the needle assembly of FIG. 17 with the deflector lever pushed forward to retract the patient end of the needle inside the needle housing.

The embodiments illustrated in the Figures are needle assemblies intended to be screwed or otherwise attached to the forward end of a syringe, cartridge or injection device to allow injection of a substance.

Figure 3:
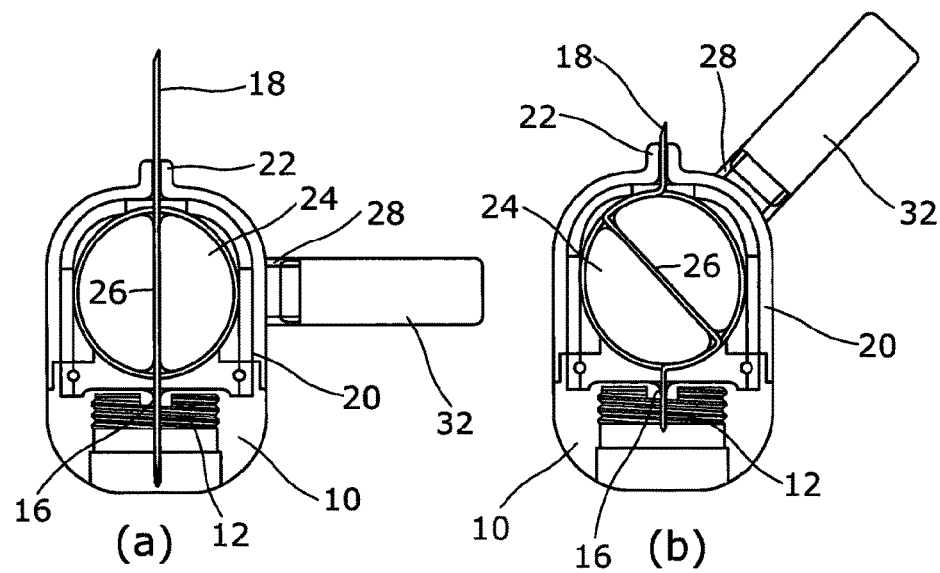
Figure 3:
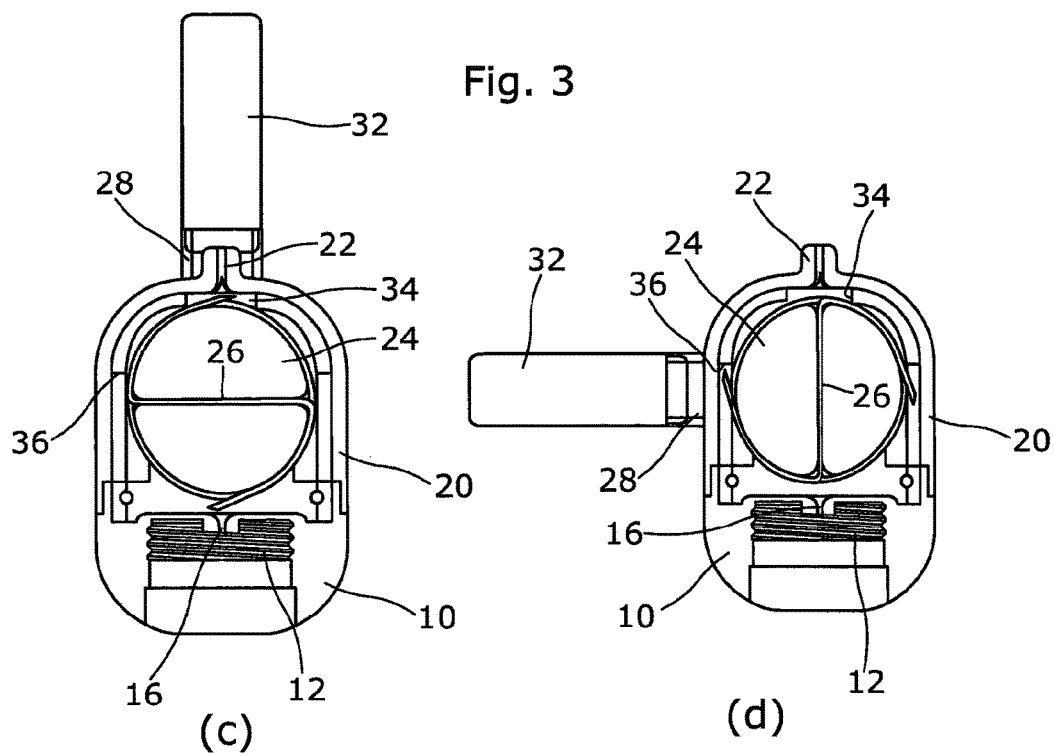

The embodiment illustrated in FIGS. 1 to 3 comprises a threaded hub portion 10 with internal threads 12 and external splines 14 and having a central eye or guide 16 which slideably receives the non-patient end of a needle 18. Extending forwardly of the hub 10 is a housing 20 clipped or otherwise secured to the needle hub 10 and defining a forward eye or guide 22 through which the patient end of the needle end 18 passes. Mounted for rotation in the housing 20 is a drum 24 of solid cylindrical form save for a narrow bore 26 extending across the diameter. In the bore is secured by adhesive or other suitable means the needle 18. Opposite ends of the drum extend outside of the housing 20 and are connected in non-rotatable fashion to the twin arms 28 of a deflector lever 30 having an actuating flap portion 32.

As seen in FIGS. 1 and 3(a), the retractable needle assembly is initially provided to the user with the needle 18 in a straight, extended condition and the flap 32 of the deflector lever projecting at an angle perpendicular to the needle axis and the axis of rotation of the drum. It is important to note that, the flap centre axis lies on a plane containing the needle axis but perpendicular to the rotational axis of the drum. Also, as seen in FIGS. 4(a) and (b), when the retractable needle assembly is attached to the front end of the syringe, cartridge or injection device, and a user places their hand around the cylindrical barrel of the syringe etc with their thumb on the centre line, it will naturally be aligned with the flap 32 thus acting as a guard for the thumb whilst the injection is carried out. When the injection is complete, the user may retract both the patient and non-patient ends of the needle simultaneously simply by pushing forwardly on the flap 32 with their thumb so that it moves from the position shown in FIG. 3(a) to that shown in FIG. 3(c).

It will be noted that, in this arrangement, one quarter turn of the drum is sufficient fully to retract the patient and non-patient ends of the needle to the inner end of each of the eyes 16 and 22 and that once the needle ends are in this condition, they cannot be re-extended by reverse operation of the flap. Although the needle is safe in this position, if required the flap may be rotated through a further 90° to the position shown in FIG. 3(d). The interior of the housing may have surfaces or shoulders 34, 36 against which a tip of the needle may come to a stop if an attempt is made to re-extend the needle.

Referring now to the second embodiment, as in the first embodiment, this comprises a hub 110 for being screwed or otherwise attached to the front end of a syringe, cartridge or other injection device by means of an internal thread 112. A needle 118 extends through a diametrical bore provided in a drum 124 and may be turned by means of a deflector lever 130 having an operating flap 132 which aligns with the thumb of a user when grasping the injection device in conventional manner. As previously, the flap may be rotated from the position shown in the Figures to a position aligned with the needle axis, to cause the needle to be wrapped around the periphery of the drum 124 and to be retracted into a housing 120.

Although this second embodiment could be formed by separately moulding the various components and connecting them together in suitable manner, the Figures shown an arrangement which is intended to be moulded as an integral moulding of plastics material which comprises sets of two regions defining the hub 110, the housing 120, the drum 124 and the deflector lever 130 which are hinged together by an integrally formed hinge 150. This allows assembly of the device simply by placing the needle 118 in a channel 126 in one of the portions $124^1$ and $124^2$ defining the drum and aligned with eye portions 116 and 122, and then closing the moulding together about the hinge 150. The drum portions $124^1$ and $124^2$ include wells 152 spaced along the needle groove 150 and also include locking spigots and bores 154, 155, which clip the two portions of the hub together. The deflector lever merges with the surface of the drum 124 and also includes snap connector features 158. The drum portions $124^1$ and $124^2$ are connected to adjacent housing portions $120^1$ and $120^2$ by means of frangible webs 160 to allow moulding and assembly. Upon operation of the device, the webs break to allow the assembled drum 124 to rotate relative to the assembled housing 120.

The hub portions 110$^1$ and 110$^2$ include snap fit connector features 162$^1$ and 162$^2$.

The deflector arm portions 130$^1$ and 130$^2$ include internally directed teeth 164$^1$, 164$^2$ which are circumferentially aligned with circular toothed tracks 168$^1$ and 168$^2$ on the outside of the housing portions 120$^1$ and 120$^2$. These provide a non-return action to prevent rotation in the direction opposite to the retraction sense. There is a single stop tooth 170$^1$ and 170$^2$ past which the teeth on the arms snap when the lever has rotated through approximately 120° to capture the lever and prevent an attempt to re-extend the needle.

Figure 4:
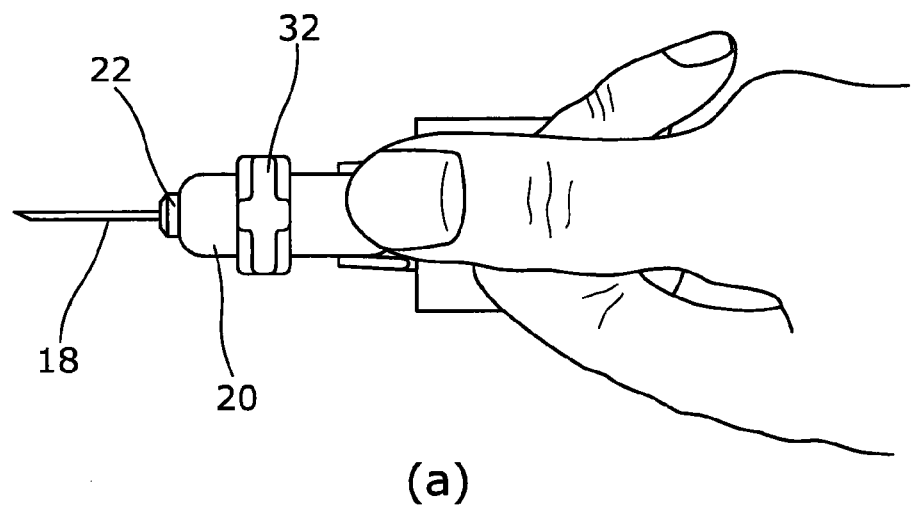
Figure 4:
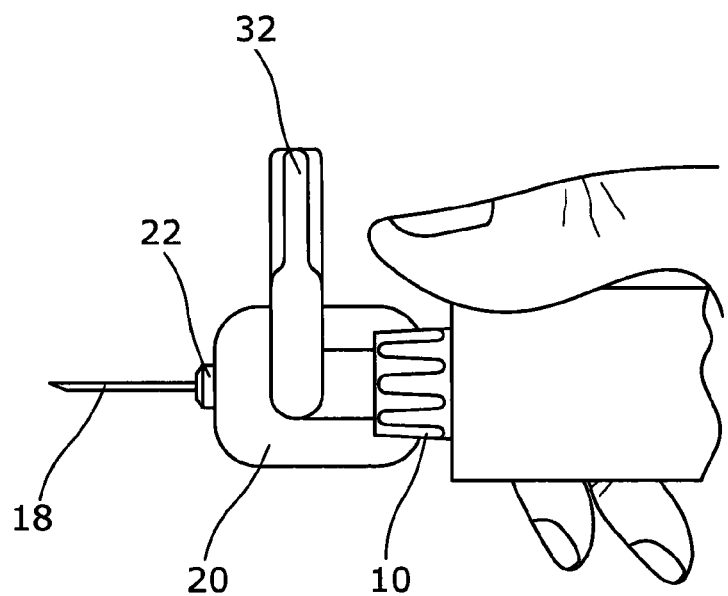
Figure 6:
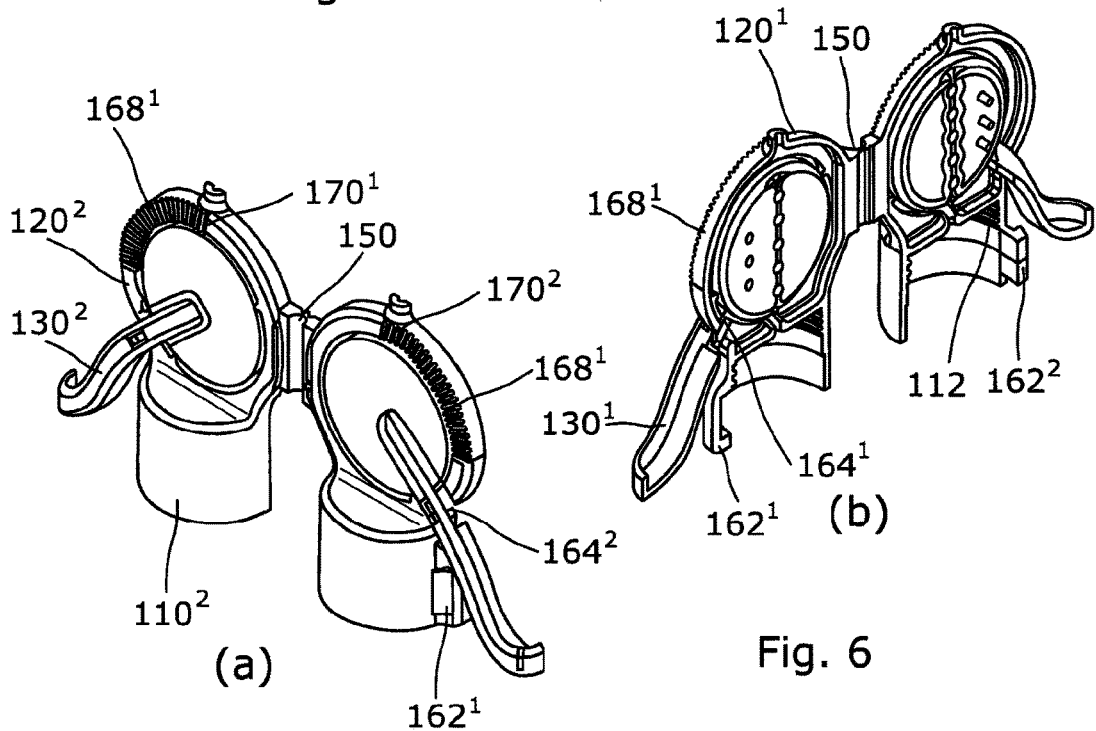
Figure 7:
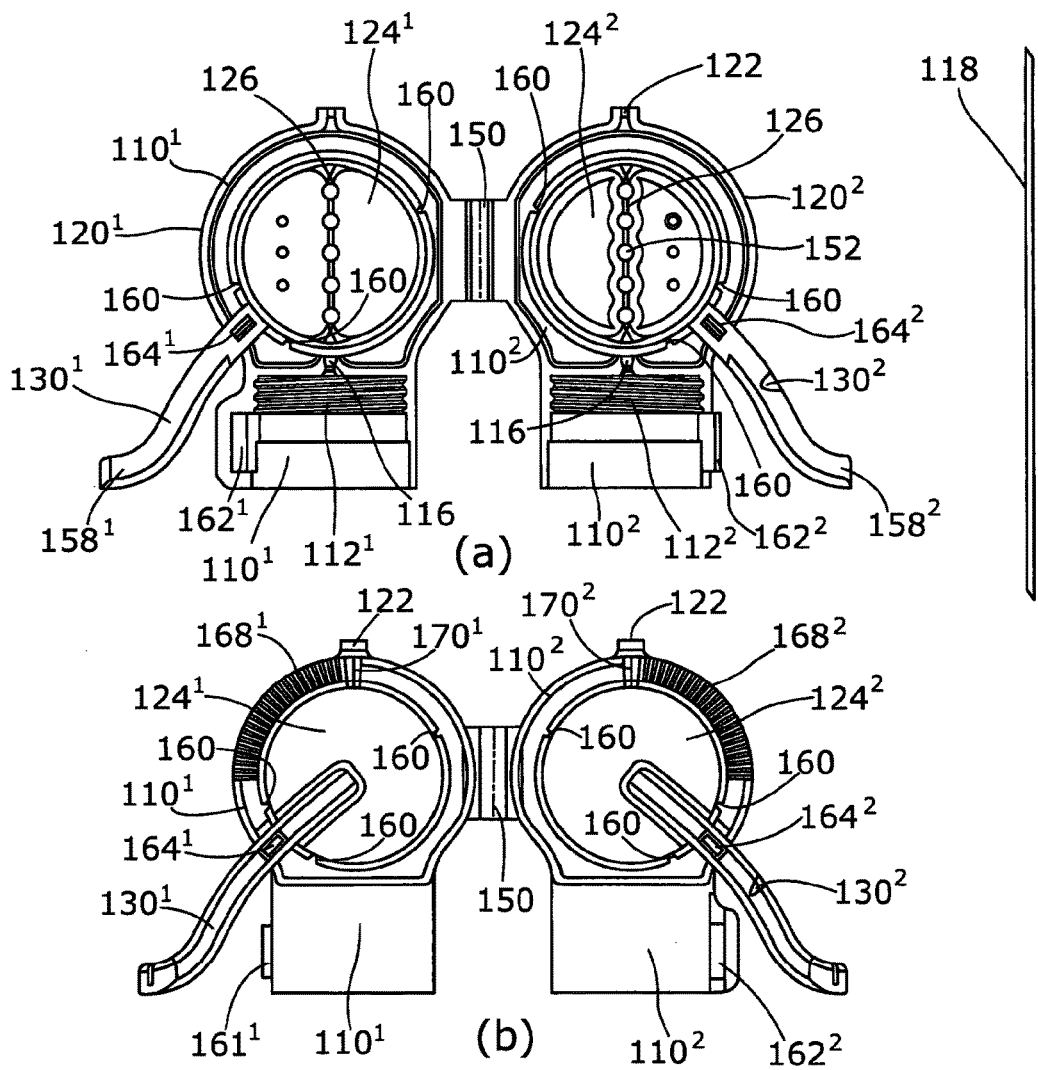

In order to manufacture and assemble the device, a preform as shown in FIGS. 6 and 7 is presented in the open condition, a needle 118 is placed in one of the grooves 126$^1$ and 126$^2$ and adhesive applied as required, and then the entire moulding is folded about the hinge 150 to bring the halves together to form the arrangement shown in FIG. 4, with the halves of each component connecting together.

After an injection, a user may flip the deflector 130 forwardly through approximately 120° to cause the needle 118 to wrap around the drum 124 as it is rotated by the deflector lever, until the needle ends are safely received within the housing and unable to re-emerge. On initial movement, the webs on the housing 160 temporarily holding the drum break to free the drum 124.

It will of course be appreciated that there are other ways in which a single integrally moulded item may be folded about one or more hinges to make up a device of the type shown in FIGS. 4 to 6.

Also, it will be appreciated that the technique of providing a single moulding with the components making up the needle assembly being in approximate halves or a plurality of complementary elements, thereby presenting a groove or other location feature for a needle to be introduced transversely, with the moulding then being closed around the needle, may be applied to other needle assemblies including those which are not retractable. Thus, in FIG. 7 there is shown a simple form of plastics moulding defining two hub parts 210$^1$ and 210$^2$ interconnected by a hinge 250 and presenting respective grooves 226$^1$ and 226$^2$ so that a needle 218 may be located into one of the grooves 226$^1$ and 226$^2$, secured, with the hub then being shut around the needle and secured by suitable features such as a snap lock 261$^1$ and 261$^2$, to provide a needle hub with an internal thread for attachment to a syringe, cartridge or injection device in the usual manner.

Referring now to FIGS. 9(*a*) to 11(*b*), as in earlier embodiments, the retractable needle assembly includes a rear portion or hub 210, for being screwed or otherwise attached to the front end of a syringe, cartridge or other injection device. A housing portion 220 is formed integrally with a forward portion of the hub 210, or alternatively the housing portion 220 can be clipped or otherwise secured onto the forward end of the hub 210 (FIG. 9(*a*)). A forward eye or guide 222 extends forwardly from the housing portion 220. A needle 218 extends forwardly from the forward eye 222.

As shown in FIG. 9(*b*), the housing 220 is provided with a recess 228 which extends into the housing 220; and a drum 224 is rotationally mounted in the recess 228 so as to be rotatable about an axis A. The forward eye 222 includes a forward needle bore 222*a*.

The drum 224 has a solid cylindrical form and includes an inner portion 224*a* and an outer portion 224*b*. The drum 224 is clipped or snap-fitted onto the housing 220. In the assembled configuration (FIG. 9(*a*)) the inner portion 224*a* is located within the recess 228 and the outer portion 224*b* is located external to the housing 220. The drum 224 is retained in the assembled configuration by inward projections 229 provided on the outer rim of the recess 228. The drum 224 includes a needle bore 227 extending through the inner portion 224*a* across its diameter. The needle bore 227 may be at least partially open on the external side of the drum 224 to allow for simple gluing or bonding of the needle 218 into the drum 224 during manufacture.

Figure 10B:
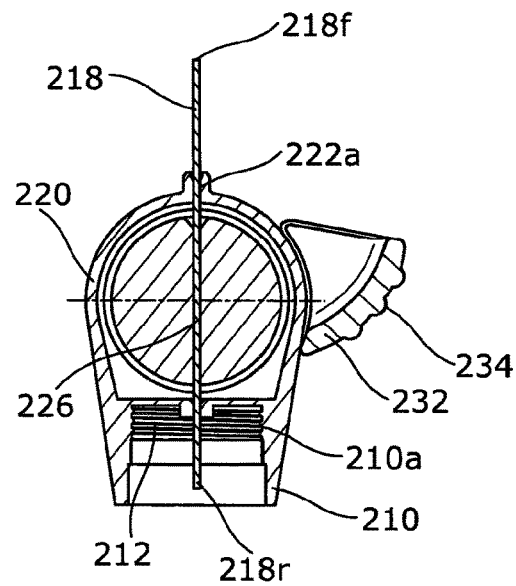

The deflection lever 230 extends from the outer portion 224*b* and projects at an angle perpendicular to the needle axis B (shown for example in FIG. 10(*a*)) and perpendicular to the axis of rotation of the drum A. A deflector lever 230 having an operating flap 232 is integrally formed with the drum 224. The operating flap 232 is provided with a grip surface 234 on its non-patient or rear surface, i.e. the surface on which the user pushes to move the lever 230. A forward facing portion of the deflector lever 230 is provided with a cavity or opening 236. When the needle assembly is in its operating position and the lever is in its first position, the cavity 236 faces the forward or patient end of the needle assembly. When the lever is in its first position, the cavity 236 is also open to the outer surface of the body portion 220 (as shown in FIGS. 9(*a*) and 9(*b*)).

FIGS. 10(*a*) and (*b*) show the retractable needle assembly in its initial operational position, as provided to the user, with the needle 218 in a straight, extended condition and the flap 232 of the deflector lever 230 in its first position. When the deflector lever is in its first position, the grip surface 234 faces essentially rearward. As such, when a user holds the device for use the grip surface faces towards the user. The needle 218 extends through the forward needle bore 222*a*, the drum needle bore 227 and a rear needle bore 210*a* in the hub 210 (FIG. 10(*b*)). An intermediate portion of the needle is secured in the drum needle bore 227 by adhesive or other suitable means.

Figure 11B:
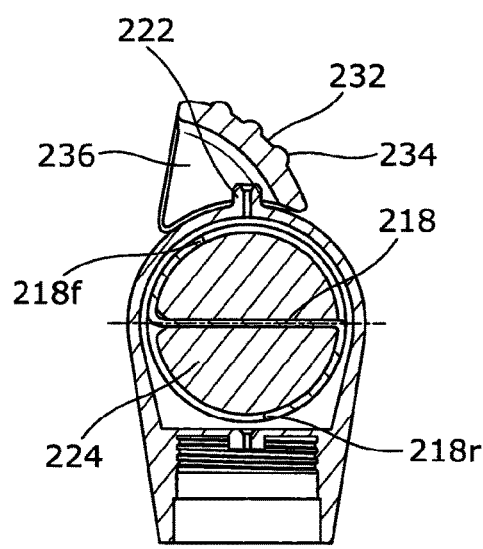

The rear portion 210 includes a threaded portion 212 for attaching the needle assembly to the front end of a syringe, cartridge or other injection device When the injection is complete, the user may retract both the patient 218*f* and non-patient ends 218*r* of the needle 218 simultaneously simply by pushing forwardly on the flap 232, for example, with their thumb or finger, so that it moves from its first position shown in FIGS. 10(*a*) and (*b*); to its second position shown in FIGS. 11(*a*) and (*b*). The grip surface 234 prevents the users thumb or finger from slipping on the operating flap 232. Alternatively, the user may rotate the lever by applying a force to the operating flap 232 in another way, for example by pushing the grip surfaces 234 against a table or other surface.

As the lever 230 and drum 224 are rotated about the axis A, the needle 218 moves from the operational position to the safe position. The drum 224 is rotated sufficiently to retract the patient end 218*f* and the non-patient end 218*r* of the needle through the bores 222*a* and 210*a*. In the safe position, the forward and rear sections of the needle 218 are wrapped around the circumference of the inner portion 224*a* of the drum. As the lever 230 rotates to its second position, the cavity 236 moves towards and covers the forward eye 222. FIG. 11(*b*) shows the lever 230 in the second position with the forward eye 222 located within the lever cavity 236. This means that when the lever 230 is in its second position, the lever 230 completely covers the forward needle bore 222*a*. This provides an additional safety feature in the case when needle 218 is not completely retracted and a portion of the forward end of the needle 218f protrudes through the bore 222a.

As with the earlier embodiments, once the needle ends are in this safe condition, they cannot be re-extended by reverse operation of the flap 232. Although the needle is safe in this position, if required the flap may be rotated further (not shown in the Figures) as described above with reference to the earlier embodiments.

FIG. 12 shows a modified version of the embodiment of FIGS. 9 to 11. In use, the operation of the embodiment is substantially the same as the preceding embodiment (and like components are indicated with corresponding reference numbers). However, it will be noted that the cavity 228' in the body portion 220' has an annular profile defined between the outer wall and a spindle 240'. The drum 224' has a corresponding annular profile so as to be received into the annular space of the cavity 228' to surround the spindle 240' (and to be rotatable about the spindle 240' in use). The spindle includes a channel 241' for receiving the needle 218'. The drum 224' also includes a pair of circumferentially opposed cut outs 225' through which the needle 218' extends when the needle assembly is fully assembled. It will be appreciated that as in the preceding embodiments rotation of the drum 224' within the cavity 226' will cause the needle 218' to be deflected and withdrawn into the body 220' (as the cut outs 226' rotate within the annular recess 228' deflecting opposing sections of the needle 218' whilst the central section of the needle 242' remains fixed in the spindle 240').

The embodiment of FIG. 12 provides an advantage in simplifying assembly. As shown in FIG. 12(b) in a first stage of assembly the needle 218' may be positioned within the housing 220' so as to extend through the forward eye or guide 222' and the channel 241' of the spindle 240' and secured in position by a convenient means such as gluing. The spindle 240' may be provided with a central opening 242' to provide a convenient gluing or bonding location. Thus, the needle 218' is fixed within the housing 220'. Subsequently the drum 224' may be snapped into position in the recess 228' of the body with the cut-outs 226' aligned with the needle 218'.

FIGS. 13 to 16 show a further embodiment, and as in earlier embodiments a retractable needle assembly includes a rear portion or hub 310 having a threaded portion 312, for being screwed or otherwise attached to the front end of a syringe, cartridge or other injection device.

The needle assembly of this embodiment is different to previous embodiments in that it comprises a forward housing portion 370 and a rear housing portion 380.

Figure 15C:
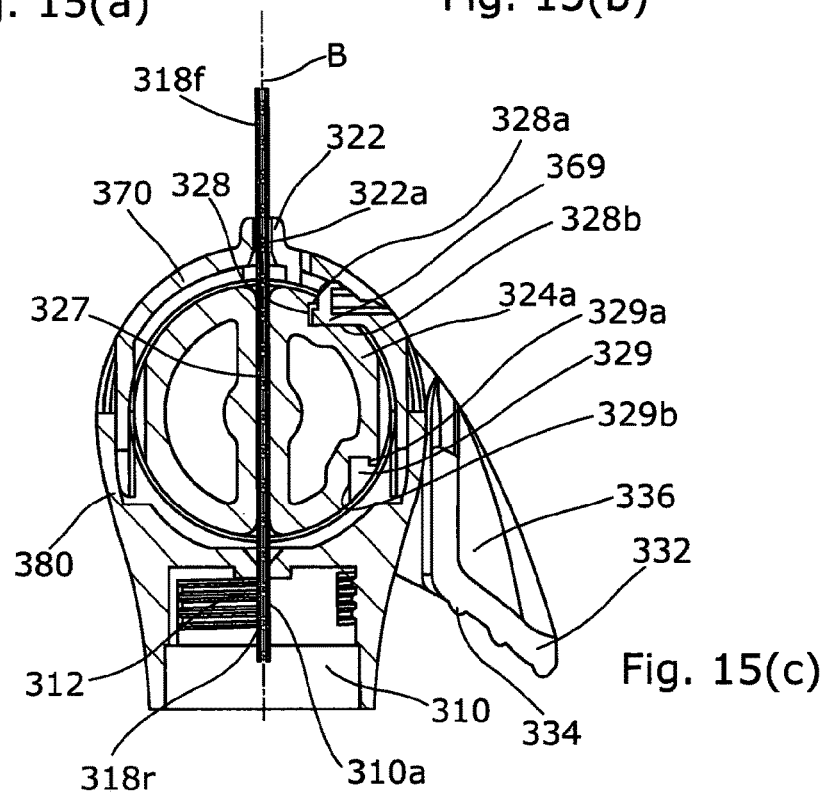

The rear housing portion 380 is formed integrally with a forward portion of the hub 310 and includes a rear needle bore 310a (FIG. 15(c)) Alternatively the rear housing portion 380 can be clipped or otherwise secured onto the forward end of the hub 310. The forward housing portion 370 includes a forward needle guide 322 and a forward needle bore 322a (FIG. 15(c)). The rear housing portion 370 and forward housing portion 380 are provided with respective engagement elements 372 and 382 (FIG. 14) which engage to hold the two portions together. In the embodiment shown, the forward housing portion 370 includes two rearwardly extending arms 372 having projections 373 which are configured to engage in two recesses 382 on the rear portion 380. Thus, it will be appreciated that the housing portions 370 and 380 may have a snap fit engagement (which is intended to be easy to assembly but difficult, or impossible, to disassembly)

When the two housing portions 370, 380 are assembled or connected (FIG. 13), they form a housing 360 having a circular recess 368 on a first side 362 which extends into the housing 360, and a drum 324 is rotationally mounted within the recess 368 so as to be rotatable about an axis A. A needle 318 is mounted in the housing and extends along a longitudinal axis B.

An inner wall of recess 368 is defined by the housing wall 364. The rear housing portion 380 includes a wall 384 having on its forward edge a semi-circular cut-out 386 (shown in FIG. 14); and the front housing portion 370 includes a wall 374 having on its rear edge a semi-circular cut-out 376 (not visible in FIG. 14). When the two housing portions 379, 380 are assembled, the two semi-circular cut-outs 376, 386 form a through-hole 365 which extends from the exterior of the housing 360 to the interior of the recess 368 (FIG. 13(b)).

The drum 324 has a cylindrical form, and includes an inner portion 324a, and an outer portion 324b from which a deflection lever 330 extends. The deflection lever 330 is essentially the same as that shown in FIGS. 9 to 11, projecting at an angle perpendicular to the needle axis B (shown for example in FIG. 15(b)) and perpendicular to the axis of rotation of the drum A. The deflection lever 330 comprises an operating flap 332 formed integrally with the drum 324. The operating flap 332 includes a cavity or opening 336 (FIG. 13(a)). The drum 324 includes a locking projection 325 which extends from the inner portion 324a along the rotation axis A. The locking projection 325 includes a stem and an enlarged head.

In the assembled configuration (FIGS. 13(a) and (b)), the inner portion 324a is located within the recess 368, and the outer portion 324b is located external to the housing 320. The stem of the locking portion is located within the hole 365, with the enlarged head located outside the housing, thereby retaining the drum 324 within the recess 368.

The embodiment of FIGS. 13 to 16 provides for simplified assembly. As can be seen from FIG. 14, the needle 318 is first inserted through the drum needle bore 327 and an intermediate portion of the needle 318 is secured in the drum needle bore 327 by adhesive or other suitable means. A patient end 318f of the needle extends from a forward part of the drum inner portion 324a and a non-patient end 318r of the needle extends from a rear part of the drum inner portion 324a. The forward housing portion 370 is moved into position surrounding the forward part of the inner portion 324a so that the patient end of the needle 318f extends through the forward needle bore 322a. The rear housing portion 380 is moved into position surrounding a forward part of the inner portion 324a so that the non-patient end of the needle 318f extends through the rear needle bore 310a. The forward and rear housing portions 370, 380 are brought into engagement around the drum 324 to form the housing 360. In the assembled configuration, the inner portion 324a is located within the recess 368 in the housing 360 and the outer portion 324b is located external to the housing 360 (FIG. 14). The stem of the locking projection 325 protrudes through the through-hole 365 in the rear of the housing 362 to retain the drum 324 within the recess 368.

In use, the operation of this embodiment is substantially the same as the preceding two embodiments. FIGS. 15(a), 15(b) and 15(c) shown the retractable needle assembly in its initial operational position, as provided to the user, with the needle 318 in a straight, extended condition and the flap 332 of the deflector lever 330 in its first position. When the injection is complete, the user may retract both the patient 318f and non-patient ends 318r of the needle 318 simultaneously simply by pushing forwardly on the flap 332 so that it moves from its first position shown in FIGS. 15(*a*) to (*c*); to its second, safe or retracted position shown in FIGS. 16(*a*) and (*b*).

In the safe position, the forward and rear sections of the needle 318*f*, 318*r* are wrapped around the outer circumference of the inner portion 324*a* of the drum. As the lever 330 rotates to its second position, the cavity 336 moves towards the forward eye 322 (FIG. 15(*c*)).

In modified versions of this embodiment (not shown), the drum can be retained in the recess using alternative retention mechanisms, for example, inward projections provided on an inner surface of the recess which engage with corresponding outward elements, such as an annular projection, provided on the drum.

As can be seen in FIGS. 15(*c*) and 16(*c*), the recess 368 is provided with an inwardly projecting resilient arm or ratchet arm 369. The arm 369 is biased towards the centre of the recess 368. The drum inner portion 324*a* is provided on its outer surface with two circumferentially spaced recesses 328, 329. When the needle assembly is in its operational position, the arm 369 is located within a first recess 328 (FIG. 15(*c*)). When the needle assembly is in its second configuration the arm is located within a second recess (FIG. 16(*c*)). Each recess 328,329 includes a locking element 338*a*, 329 on a first side, which engages with a shoulder on the arm 369 to prevent the drum 324 from rotating in an anti-clockwise direction. Each recess 328, 329 also includes a sloping surface 328*b* opposite the locking element 328*a*.

When the needle assembly is in the safe position, the arm 369 is held in the first recess 328 holding the drum is held against rotation. This means that the needle 318 remains stationary in its operational during the injection process. When the user pushes on the lever 330, the arm 369 is urged out of engagement with the first recess 329*a*, the sloping surface 328*b* acting to cam the arm 369 away from the drum 324 allowing the drum to rotate. As the lever 330 is moved to its second position, the arm 369 aligns with the second recess 329 and is urged into engagement with the second recess. This means that the needle assembly is securely held in the safe configuration.

FIG. 13(*b*) shows a cap 390 which can be fitted to the needle assembly prior to use, to protect the user from needle stick injury. The cap 390 is shaped to fit over the forward end of the needle 318*f* and at least a part of the housing 360. Although only described in this embodiment, it will be appreciated that a similar cap could be provided for all embodiments described above.

FIGS. 17 to 20 show a further embodiment of the invention. As shown in FIG. 18, a retractable needle assembly includes a rear portion or hub 410 having a threaded portion 412, for being screwed or otherwise attached to the front end of a syringe, cartridge or other injection device. A housing portion 420 is clipped or otherwise secured onto the forward end of the hub 410 (FIG. 19(*a*)). The housing portion 420 is of generally cylindrical form and defines an inner chamber 428. A longitudinal slot 468 extends along one side of the housing 420. A forward eye or guide 422 extends forwardly from the housing portion 420. A needle 418 extends forwardly from the forward eye 422 along a needle axis B.

As can be seen for example in FIG. 19(*b*), a deflector element 424 is provided in the chamber 428. The deflector element 424 is rotatably mounted in the chamber 428, for rotation about an axis A. In the embodiment shown, the deflector element 424 is provided with an axially extending central shaft 427 (FIG. 18) which is rotatably mounted in the chamber.

The deflector element 424 it includes a needle bore 426 extending across its diameter. The needle bore 426 may be at least partially open on the external side of the deflector element 424 to allow for simple gluing or bonding of the needle 318 during manufacture. The deflector element 424 is in the form of a gear wheel having teeth 425 extending from its outer circumferential surface.

The needle assembly includes a deflector lever 430 with an operating flap 432 which extends outwardly from the housing 420 through the slot 468. The operating flap 432 projects at an angle perpendicular to the needle axis B (shown for example in FIG. 19(*b*)). As with earlier embodiments, the lever operating flap 232 intersects the plane perpendicular to the deflector rotary axis A and containing the needle axis B. The deflector lever 430 includes an inner portion 440, which is being mounted within the chamber 428. The inner portion 440 is connected to or integrally formed with the flap 423. The inner portion 440 is a longitudinally extending element 440 having on a surface facing the deflector element 424*a* set of teeth 442 or rack. The teeth 442 engage with the teeth 425, thereby connecting the deflector lever 430 to the deflector element 424. This forms a rack and pinion linear actuator. When the deflector lever is pushed forward, the translational movement of the rack 442 is causes the deflector element (pinion) to rotate.

FIGS. 19(*a*) and 19(*b*) show the retractable needle assembly in its initial, operational position, as provided to the user. The deflector lever 430 is in its first position; with a forward end of the rack 442 engaged with the deflector element teeth 425. The needle 818 extends through the forward needle bore 422*a*, the drum needle bore 426 and a rear needle bore 410*a* in the hub 4210 (FIG. 19(*b*)). An intermediate portion of the needle is secured in the drum needle bore 426 by adhesive or other suitable means.

When the injection is complete, the user may retract both the patient 318*f* and non-patient ends 318*r* of the needle simultaneously simply by pushing forwardly on a rear surface of the flap 432, so that it moves from its first position shown in FIGS. 10(*a*) and (*b*); to its second position shown in FIGS. 20(*a*) and (*b*). The forward motion of the rack 442 is translated into rotational movement of the deflector element 424, drawing the patient and non-patient ends needle ends 318*f*, 318*r* into the housing and wrapping them around the deflector element (FIG. 20(*b*)).

In a modified embodiment (not shown), the housing and deflector lever are provided with cooperating features which releasably engage when the needle assembly is in the operational position to prevent the lever from being accidentally pushed forward. In a further modified embodiment (not shown), the housing and deflector lever are provided with cooperating features, for example, a ratchet arm and recess, which engage when the needle assembly is in the safe position to ensure the needle is retained securely in the housing.

With all of the embodiments described above, when the retractable needle assembly is in its safe configuration, the user can safely remove the needle assembly from the injection device and dispose of it.

Although only described for some of the embodiments, it will be appreciated that all embodiments of the invention could be provided with cooperating features on the housing and deflector element which are configured to retain or lock the deflector element in its rotated position, or in other words when the needle is in its safe position, to lock the needle assembly in its safe configuration. Such cooperating features function as a non-return mechanism.

In the same way, the deflector element and housing could be provided with cooperating features which releasably hold the deflector and needle in the operational position. The cooperating features being released when sufficient force is applied to the deflector lever so that the user can retract the needle.

The interior wall of the recess may have surfaces or shoulders (not shown) against which a tip of the needle may come to a stop if an attempt is made to re-extend the needle.

The needle assembly may also be provided with an indicator (not shown) which provides at least one of a tactile, an audible and a visual indication that the needle is safely retracted.

We claim:

1. A retractable needle assembly comprising:
   a body portion;
   a needle having a patient end and being movable between an operational position in which the needle extends along a longitudinal needle axis with the patient end projecting forwardly from the body portion, and a safe position in which the patient end is retracted into the body portion;
   a deflector element rotatable about a deflector rotary axis generally perpendicular to the longitudinal needle axis to move the needle to its safe position, and
   a manually operated deflector lever connected to or forming part of the deflector element, the manually operated deflector lever projecting from the body portion and intersecting a plane perpendicular to the deflector rotary axis and containing the longitudinal needle axis, the manually operated deflector lever rotates about the deflector rotary axis, from a first position perpendicular to the longitudinal needle axis to a second position parallel to the longitudinal needle axis, to fully retract the needle.

2. The retractable needle assembly according to claim 1, wherein the deflector element comprises a rotary element through which an intermediate portion of the needle extends and about a circumference which the needle is wound when the deflector element is rotated.

3. The retractable needle assembly according to claim 2, wherein the circumference of the rotary element and a length of the needle are selected so that the patient end of the needle is retracted into the body portion upon rotation of the rotary element by an angular amount of 270° or less.

4. The retractable needle assembly according to claim 3, wherein the circumference of the rotary element and the length of the needle are selected so that the patient end of the needle is retracted into the body portion upon rotation of the rotary element by an angular amount of less than 180°, preferably less than 120° and, ideally, by about 90°.

5. The retractable needle assembly according to claim 1, wherein the manually operated deflector lever projects transversely relative to the longitudinal needle axis.

6. The retractable needle assembly according to claim 5, wherein the manually operated deflector lever projects at an angle of at least 90° to the patient end of the needle.

7. The retractable needle assembly according to claim 1, wherein the needle is double ended with a non-patient end opposite the patient end configured in use for piercing a seal element.

8. The retractable needle assembly according to claim 7, wherein the deflector element causes both ends of the needle to retract into the body portion upon rotation thereof.

9. The retractable needle assembly according to claim 7, wherein the non-patient end is fixed and the deflector element causes the patient end only to retract.

10. The retractable needle assembly according to claim 1, including a non-return mechanism for preventing movement of the manually operated deflector lever in a direction opposite to that which causes retraction, over at least part of its arc of rotation.

11. The retractable needle assembly according to claim 1, which includes a snap-action end stop which operates to permanently capture the manually operated deflector lever at a end of a retraction stroke and to provide a sensory indication to a user that the needle is safe.

12. The retractable needle assembly according to claim 1, comprising a moulded plastics item for connecting around the needle.

13. The moulded plastics item according to claim 12, including first and second drum portions configured to be brought together in use about the needle to provide a drum with the needle extending therethrough.

14. The moulded plastics item according to claim 13, including first and second housing portions configured to be brought together in use to provide a housing defining a generally circular opening in which the drum is constrained to rotate.

15. The moulded plastics item according to claim 14, wherein at least one of the first and second drum portions is connected to respective first and second housing portions by frangible webs.

16. The moulded plastics item according to claim 12, including first and second connector portions configured to be brought together in use to form a connector to allow the retractable needle assembly to be connected in use directly or indirectly to at least one of a syringe, cartridge, or injection device.

* * * * *